US010292681B2

(12) United States Patent
Park et al.

(10) Patent No.: US 10,292,681 B2
(45) Date of Patent: May 21, 2019

(54) ULTRASOUND IMAGE PROVIDING APPARATUS AND METHOD

(71) Applicant: SAMSUNG MEDISON CO., LTD., Hongcheon-gun, Gangwon-do (KR)

(72) Inventors: Seok-lai Park, Hongcheon-gun (KR); Jae-moon Jo, Seongnam-Si (KR); Ji-un Im, Hongcheon-gun (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 819 days.

(21) Appl. No.: 14/692,381

(22) Filed: Apr. 21, 2015

(65) Prior Publication Data

US 2016/0157824 A1 Jun. 9, 2016

(30) Foreign Application Priority Data

Dec. 5, 2014 (KR) ........................ 10-2014-0174279

(51) Int. Cl.
 *A61B 8/00* (2006.01)
 *G01S 7/52* (2006.01)
(52) U.S. Cl.
 CPC .............. *A61B 8/467* (2013.01); *A61B 8/463* (2013.01); *A61B 8/464* (2013.01); *A61B 8/465* (2013.01); *G01S 7/52033* (2013.01); *G01S 7/52074* (2013.01); *G01S 7/52084* (2013.01); *A61B 8/4405* (2013.01)
(58) Field of Classification Search
 CPC ......... A61B 8/463; A61B 8/464; A61B 8/467; A61B 8/465; A61B 8/4405; G01S 7/52033; G01S 7/52074; G01S 7/52084
 See application file for complete search history.

(56) References Cited

U.S. PATENT DOCUMENTS

| 5,482,045 A | 1/1996 | Rust et al. |
|---|---|---|
| 2009/0069682 A1 | 3/2009 | Hastings et al. |
| 2011/0043434 A1 | 2/2011 | Roncalez et al. |
| 2012/0136253 A1 | 5/2012 | Kim et al. |
| 2013/0249842 A1 | 9/2013 | Varna |
| 2013/0303911 A1 | 11/2013 | Lee et al. |

(Continued)

FOREIGN PATENT DOCUMENTS

| EP | 2 710 960 A1 | 3/2014 |
|---|---|---|
| EP | 2742868 A1 | 6/2014 |

(Continued)

OTHER PUBLICATIONS

Extended European Search Report issued in European Application No. 15160032, dated Jun. 8, 2016.

*Primary Examiner* — Bo Joseph Peng
(74) *Attorney, Agent, or Firm* — Morgan Lewis & Bockius LLP

(57) ABSTRACT

Disclosed are an ultrasound image providing apparatus and method. The ultrasound image providing apparatus includes an interface that displays a screen including a gain setting window which includes a plurality of slide bars for setting a plurality of time gain compensation (TGC) values of ultrasound image data, and receives, through the gain setting window, a user input for adjusting at least one selected from the sizes and number of slide bars, and a controller that performs control to update and display the gain setting window, based on the user input.

11 Claims, 15 Drawing Sheets

(56) References Cited

U.S. PATENT DOCUMENTS

| | | | |
|---|---|---|---|
| 2014/0088428 A1* | 3/2014 | Yang | A61B 8/4444 600/443 |
| 2014/0113268 A1* | 4/2014 | Dhasmana | G06Q 10/1091 434/365 |
| 2014/0164965 A1 | 6/2014 | Lee et al. | |
| 2015/0057541 A1* | 2/2015 | Yang | A61B 8/4444 600/437 |

FOREIGN PATENT DOCUMENTS

| | | |
|---|---|---|
| JP | 2005-074028 A | 3/2005 |
| KR | 10-2008-0051917 A | 6/2008 |
| KR | 10-2012-0056323 A | 6/2012 |
| KR | 10-2014-0039954 A | 4/2014 |
| KR | 10-2014-0090283 A | 7/2014 |
| WO | WO 2008034799 A1 * | 3/2008 ........... G06F 19/321 |

* cited by examiner

ULTRASOUND IMAGE PROVIDING APPARATUS AND METHOD

RELATED APPLICATION

This application claims the benefit of Korean Patent Application No. 10-2014-0174279, filed on Dec. 5, 2014, in the Korean Intellectual Property Office, the disclosure of which is incorporated herein in its entirety by reference.

BACKGROUND

1. Field

One or more exemplary embodiments relate to an ultrasound image providing apparatus and method, and more particularly, to an ultrasound image providing apparatus which includes a user interface for setting a time gain compensation (TGC) value and an ultrasound image providing method.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissue or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including computed tomography (CT) apparatuses, magnetic resonance imaging (MRI) apparatuses, and the like.

Generally, in an ultrasound beam which passes through tissue, the amplitude or intensity thereof is reduced depending on a propagation distance. In regard to attenuation, as a distance through which the ultrasound beam passes increases, amplitude is more reduced. The intensity of an ultrasound response signal (an echo signal) received by attenuation is not constant. That is, an ultrasound image based on the ultrasound response signal may not have uniform brightness, or the qualities of some ultrasound images may not be good. Therefore, it is required to develop a system which enables a user to easily compensate for the sensitivity of an ultrasound image.

SUMMARY

Additional aspects will be set forth in part in the description which follows and, in part, will be apparent from the description, or may be learned by practice of the presented exemplary embodiments.

According to one or more exemplary embodiments, an ultrasound image providing apparatus includes: an interface that displays a screen including a gain setting window which includes a plurality of slide bars for setting a plurality of time gain compensation (TGC) values of ultrasound image data, and receives, through the gain setting window, a user input for adjusting at least one selected from the sizes and number of slide bars; and a controller that performs control to update and display the gain setting window, based on the user input.

When the gain setting window is updated based on the user input, the controller may update positions of a plurality of adjustment buttons displayed on the plurality of slide bars.

On the plurality of slide bars, a position of each of the plurality of adjustment buttons may correspond to a TGC value.

The interface may include a touch screen.

The gain setting window may include the plurality of slide bars which are arranged along a vertical axis, and the vertical axis may indicate a depth of an ultrasound image.

The interface may receive a user input for increasing or decreasing a horizontal-direction length of each of the plurality of slide bars.

The interface may receive a user input for increasing or decreasing the number of slide bars.

The interface may receive a user input for increasing or decreasing the number of slide bars in a certain section of the vertical axis.

The interface may receive a user input for enlarging and displaying the ultrasound image, and the controller may perform control to increase and display the number of slide bars.

The controller may perform control to change and display at least one selected from sizes and number of the plurality of slide bars according to a size of the interface.

The plurality of TGC values respectively corresponding to the plurality of slide bars may be displayed as numbers.

When the gain setting window is updated based on the user input, the controller may update the plurality of TGC values respectively displayed on the plurality of slide bars.

According to one or more exemplary embodiments, an ultrasound image providing apparatus includes: a display that displays a screen including a gain setting window which includes a plurality of slide bars for setting a plurality of time gain compensation (TGC) values of ultrasound image data; a user input receiving unit that receives, through the gain setting window, a user input for adjusting at least one selected from sizes and number of the plurality of slide bars; and a controller that performs control to update and display the gain setting window, based on the user input.

The controller may perform control to display the gain setting window in an interface of an external device that operates in connection with the ultrasound image providing apparatus, and adjust at least one selected from sizes and number of the plurality of slide bars, displayed in the interface of the external device, according to a size of the interface of the external device.

According to one or more exemplary embodiments, an ultrasound image providing method includes: displaying a screen including a gain setting window which includes a plurality of slide bars for setting a plurality of time gain compensation (TGC) values of ultrasound image data; receiving, through the gain setting window, a user input for adjusting at least one selected from the sizes and number of slide bars; and performing control to update and display the gain setting window, based on the user input.

The performing of the control may include, when the gain setting window is updated based on the user input, updating positions of a plurality of adjustment buttons displayed on the plurality of slide bars.

On the plurality of slide bars, a position of each of the plurality of adjustment buttons may correspond to a TGC value.

The displaying may include displaying the gain setting window that includes the plurality of slide bars which are arranged along a vertical axis, and the vertical axis may indicate a depth of an ultrasound image.

The receiving of the user input may include receiving a user input for increasing or decreasing a horizontal-direction length of each of the plurality of slide bars.

The receiving of the user input may include receiving a user input for increasing or decreasing the number of slide bars.

The receiving of the user input may include receiving a user input for increasing or decreasing the number of slide bars in a certain section of the vertical axis.

The receiving of the user input may include receiving a user input for enlarging and displaying the ultrasound image, and the performing of the control may include performing control to increase and display the number of slide bars.

According to one or more exemplary embodiments, a non-transitory computer-readable storage medium stores a program for executing the ultrasound image providing method according to an exemplary embodiment.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
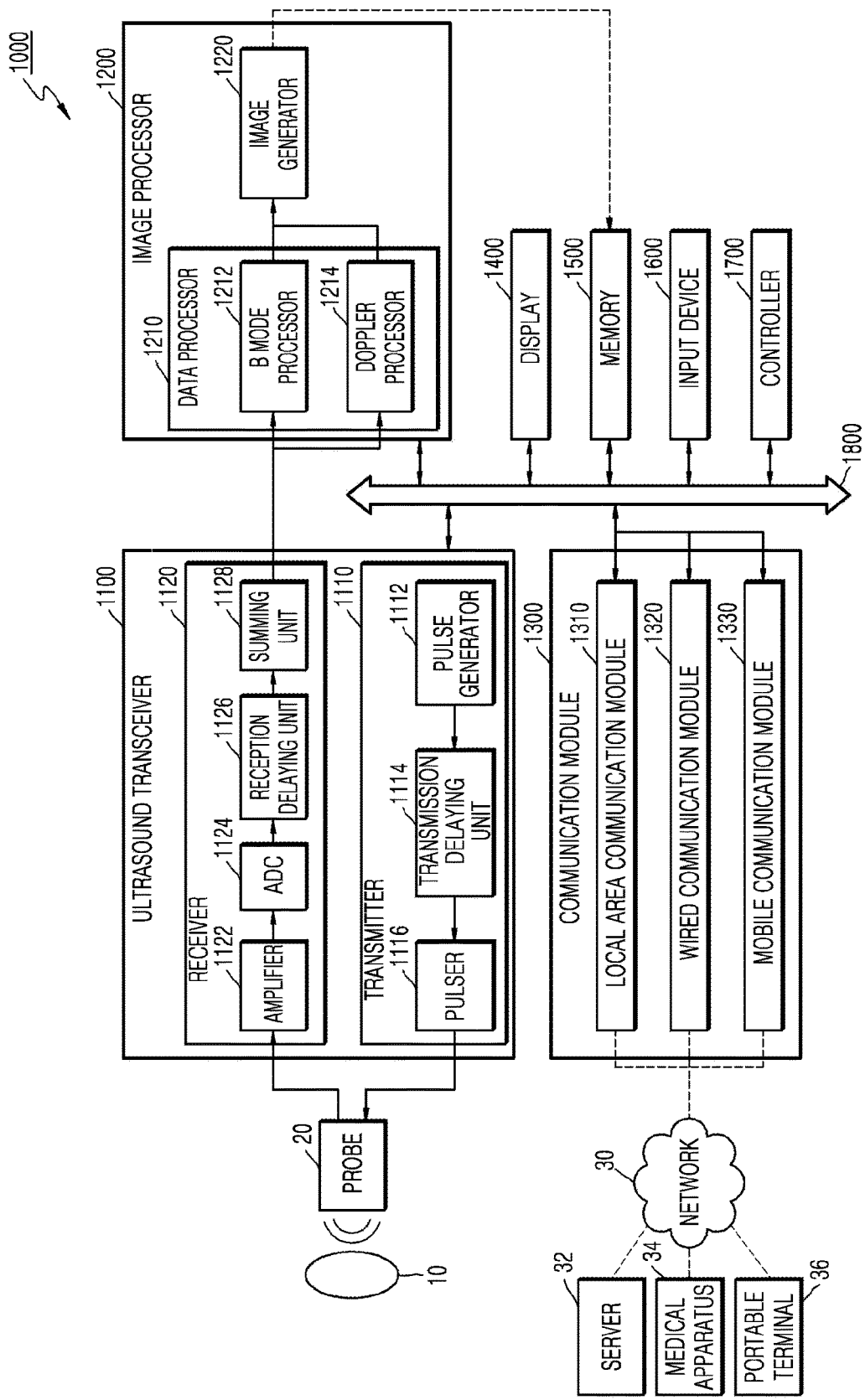
FIG. 1 is a block diagram illustrating a configuration of an ultrasound diagnosis apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Furthermore, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Embodiments of the invention now will be described more fully hereinafter with reference to the accompanying drawings, in which illustrative embodiments of the invention are shown.

FIG. 1 is a block diagram illustrating a configuration of an ultrasound diagnosis apparatus 1000 according to an exemplary embodiment. Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly.

A transmitter 1110 supplies a driving signal to the probe 20. The transmitter 1110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

When a touch pad forms a layer structure along with a display panel to configure a touch screen, the display 1400 may perform a function of an input device 1600 in addition to a function of an output unit.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. However, embodiments are not limited thereto, and some of the components stated above may be implemented as hardware modules. Furthermore, at least one selected from the ultrasound transceiver 1100, the image processor 1200, and the communication module 1300 may be included in the controller 1700. However, embodiments are not limited thereto.

FIG. 2 is a block diagram for describing an ultrasound image providing apparatus 200 according to an exemplary embodiment.

The ultrasound image providing apparatus 200 denotes an electronic apparatus that performs at least one selected from acquiring, processing, and displaying of an ultrasound image. In detail, the ultrasound image providing apparatus 200 according to an exemplary embodiment denotes an apparatus that provides a user with a GUI for setting a gain value used to generate an ultrasound image.

Figure 2A:
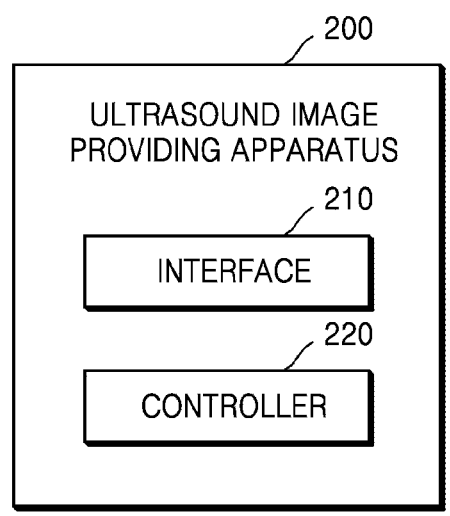
FIG. 2A-FIG. 2B are block diagrams for describing an ultrasound image providing apparatus according to an exemplary embodiment.

Referring to FIG. 2A, the ultrasound image providing apparatus 200 may include an interface 210 and a controller 220.

The ultrasound image providing apparatus 200 of FIG. 2A may be included in the ultrasound diagnosis apparatus 1000 described above with reference to FIG. 1, or may operate in connection with the ultrasound diagnosis apparatus 1000.

When the ultrasound image providing apparatus 200 of FIG. 2A is included in the ultrasound diagnosis apparatus 1000 of FIG. 1, the interface 210 and the controller 220 may respectively correspond to the display 1400 and controller 1700 of FIG. 1.

When the ultrasound image providing apparatus 200 operates in connection with the ultrasound diagnosis apparatus 1000, the ultrasound image providing apparatus 200 may be included in the medical apparatus 34 or the portable 36 which is connected to the ultrasound diagnosis apparatus 1000 over the network 30 of FIG. 1.

The interface 210 may display information processed by the ultrasound image providing apparatus 200. For example, the interface 210 may display an ultrasound image of an object on a screen and display a user interface (UI) or a GUI associated with setting a function. As described above, the interface 210 may include a touch screen in which a display panel and a touch pad form a layer structure. When the interface 210 includes a touch screen, the interface 210 may receive a user input.

Figure 4A:
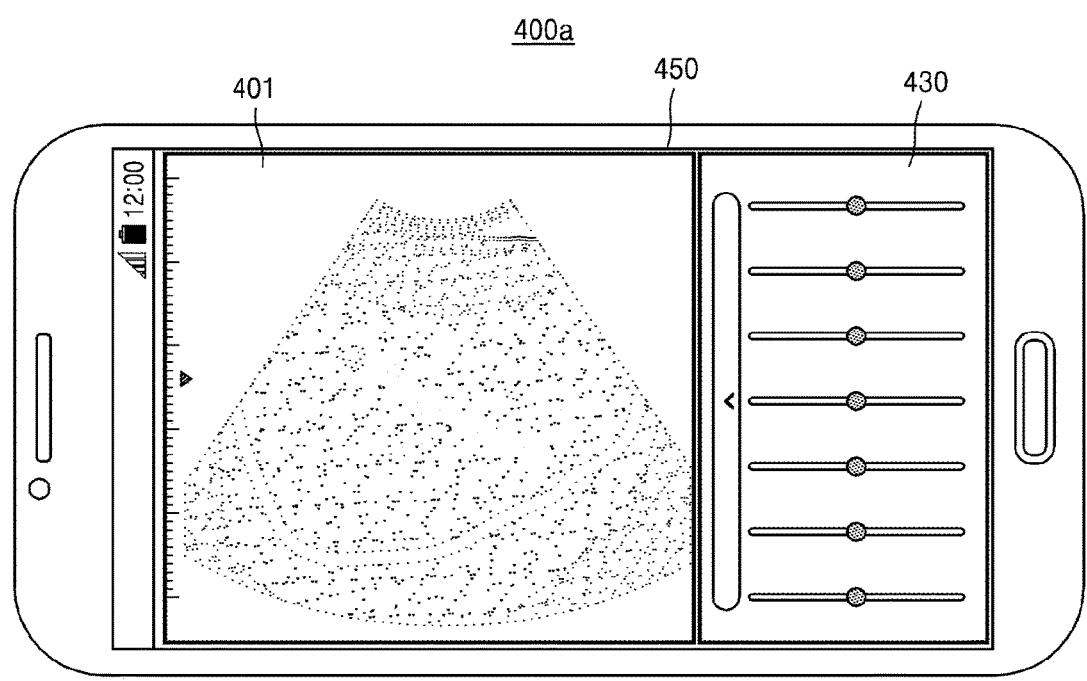
FIG. 4A-FIG. 4E are block diagrams for describing an interface which displays a screen including a gain setting window.
Figure 4B:
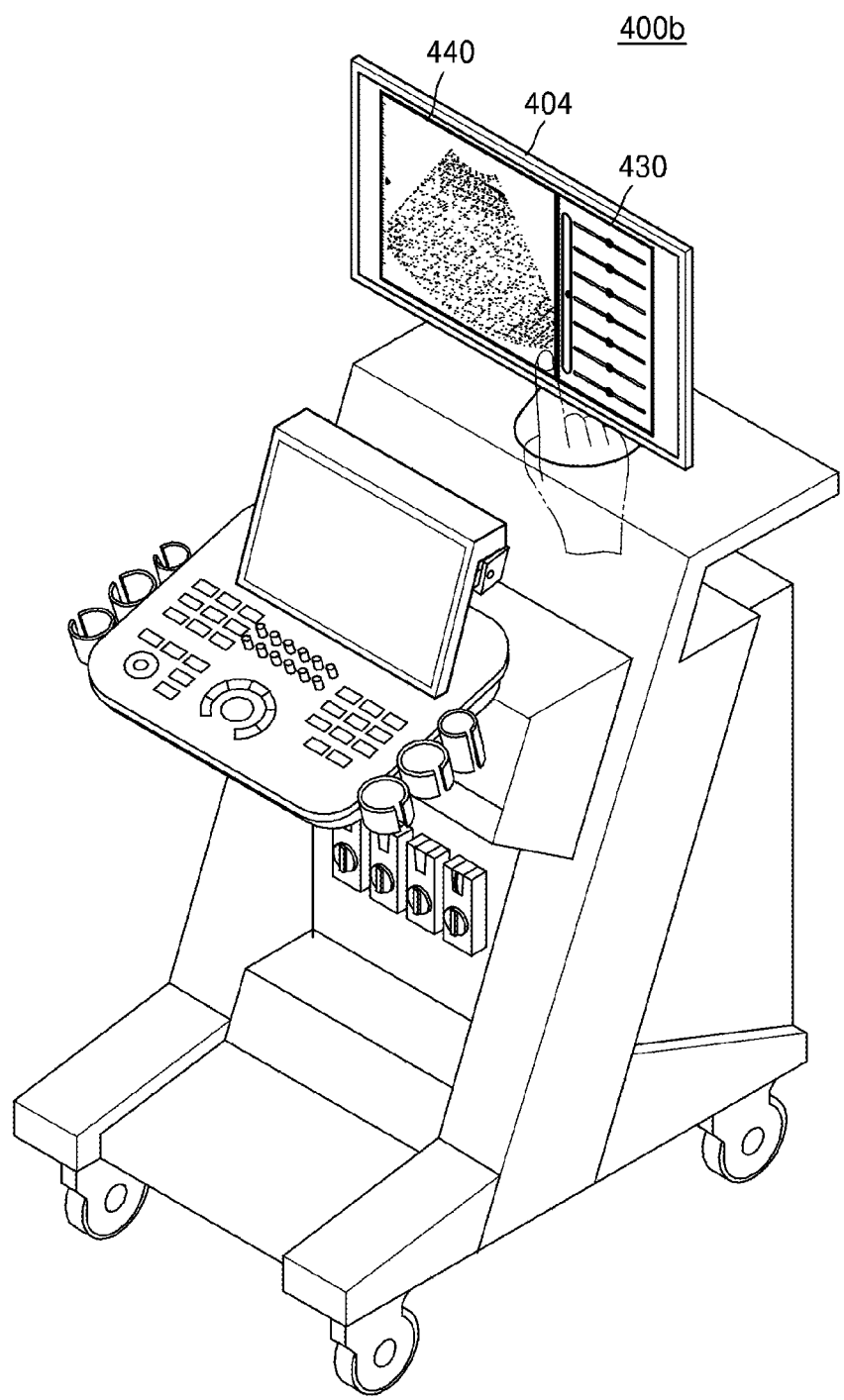
Figure 4C:
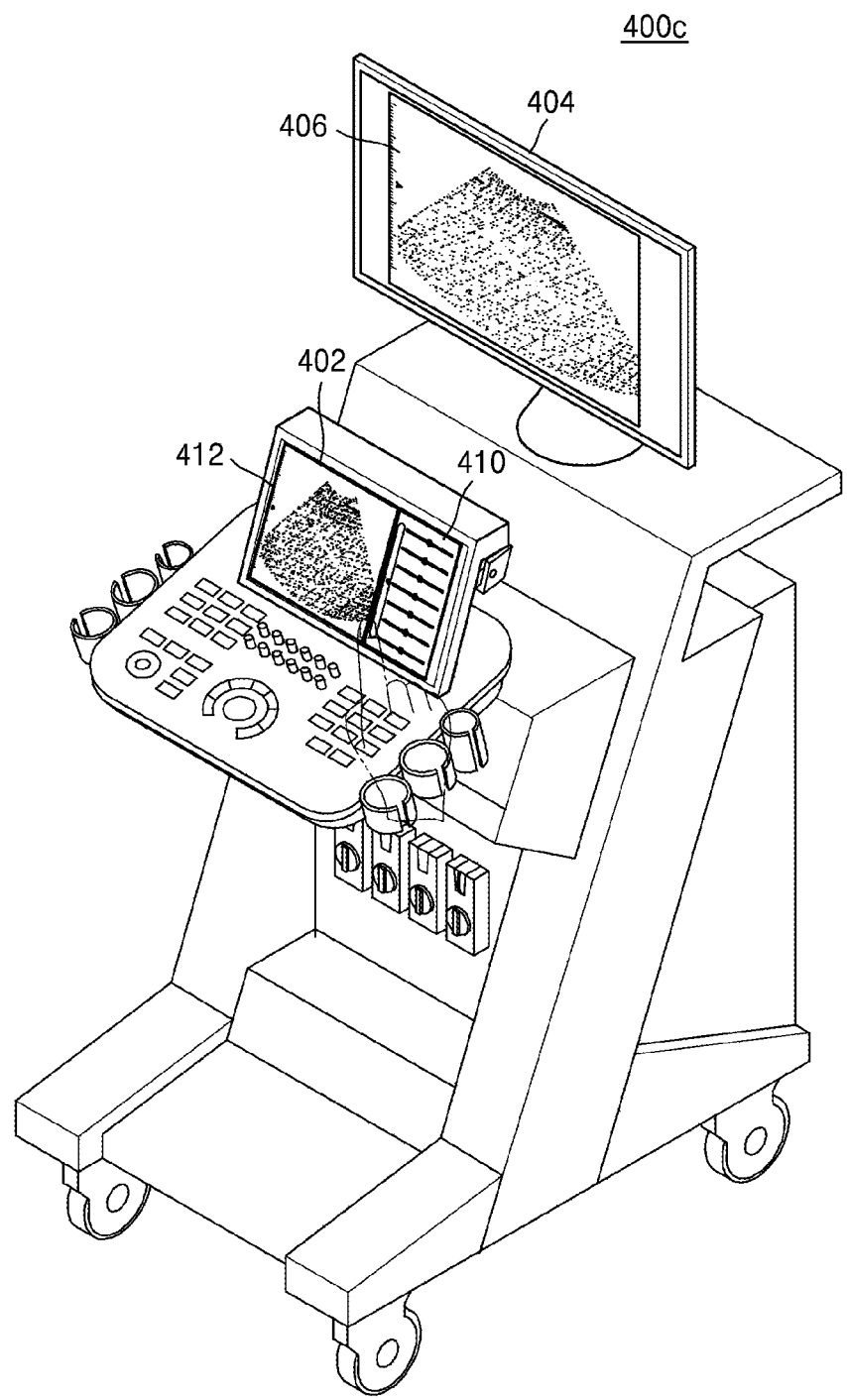

For example, as illustrated in FIG. 4A, the interface 210 may be a display 450 of a portable ultrasound image providing apparatus 400a. As another example, as illustrated in FIG. 4B, the interface 210 may be a display 404 that displays an ultrasound image generated by a cart-type ultrasound image providing apparatus 400b. As another example, as illustrated in FIG. 4C, the interface 210 may be a display 402 which is provided in a control panel of a cart-type ultrasound image providing apparatus 400c separately from the display 404.

The interface 210 may display a screen including a gain setting window that includes a plurality of slide bars for setting a plurality of time gain compensation (TGC) values of ultrasound image data. Each of the TGC values denotes a value that is used to compensate for a level of an ultrasound signal being reduced according to a depth of a human body. A user may use a plurality of slide bars, for differently setting a TGC value for each depth of an ultrasound image. In an ultrasound image, a depth value may increase in a direction from a boundary surface to soft tissue of a diagnosis target, which is diagnosed by the ultrasound diagnosis apparatus 1000.

A plurality of slide bars 502 (see FIG. 5) according to an exemplary embodiment may be arranged in a gain setting window along a vertical axis. The vertical axis may indicate a depth of an ultrasound image.

The interface 210, as illustrated in FIG. 4A, may display a screen that includes a gain setting window 430 and an ultrasound image 401 to which a plurality of TGC values are applied. Detailed exemplary embodiments in which a screen including a gain setting window is displayed will be described below with reference to FIGS. 4A to 4E.

The interface 210 may receive, through a gain setting window, a user input for adjusting at least one selected from the sizes and number of slide bars. According to an exemplary embodiment, the interface 210 may include a touch screen. When the interface 210 is implemented with a touch screen, the interface 210 may sense a touch input which is performed on a screen by a stylus pen or a finger.

In detail, the touch screen may output a user interface screen and receive a user input through the output user interface screen. In detail, the touch screen includes a touch pad (not shown) coupled to a display panel (not shown), and outputs the user interface screen onto the display panel. When the user touches a certain point of the user interface screen, the touch pad senses the touched point to recognize a certain command input by the user.

The touch screen may display a user interface screen which includes an ultrasound image, acquired based on data which is acquired through ultrasound scan, and a gain window for setting a TGC value.

In detail, the interface 210 may sense a touch input by using a contact capacitive type, a press resistive type, an infrared sensing type, a surface ultrasound conductive type, an integration tension measurement type, or a piezo effect type. The touch input may be received based on a touch gesture. Here, examples of the touch gesture may include a tap, a touch and hold, a double tap, a drag, panning, a flick, a drag and drop, a swipe, a press, and a press and tap.

The controller 220 may perform control to update and display a gain setting window, based on a user input. For example, the controller 220 may increase or decrease the number of slide bars included in the gain setting window, based on the user input. Also, the controller 220 may increase or decrease the number of slide bars in a first section of a vertical axis, based on the user input. A detailed exemplary embodiment for updating and displaying a gain setting window will be described in detail with reference to FIGS. 5 to 8.

Figure 2B:
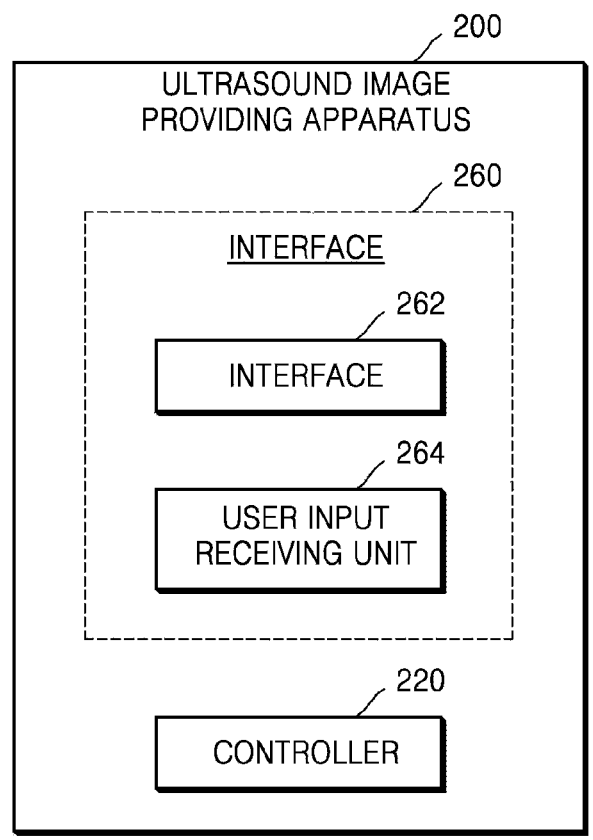

Referring to FIG. 2B, an ultrasound image providing apparatus 250 according to another exemplary embodiment may include an interface 260 and a controller 270.

Operations respectively performed by the interface 260 and the controller 270 illustrated in FIG. 2B are the same as operations respectively performed by the interface 210 and the controller 220 described above with reference to FIG. 2A. Therefore, the same descriptions provided with regard to the interface 210 and the controller 220 are not repeated.

A display 262 and a user input receiving unit 264 of the interface 260 of FIG. 2B may respectively perform operations performed by the interface 210 of FIG. 2A.

In detail, the display 262 may display a screen including a gain setting window that includes a plurality of slide bars for setting a plurality of TGC values of ultrasound image data. For example, as illustrated in FIG. 4A, the display 262 may be the display 450 of the portable ultrasound image providing apparatus 400a. As another example, as illustrated in FIG. 4B, the display 262 may be the display 404 that displays an ultrasound image generated by the cart-type ultrasound image providing apparatus 400b. As another example, as illustrated in FIG. 4C, the display 262 may be the display 402 which is provided in the control panel of the cart-type ultrasound image providing apparatus 400c separately from the display 404. The display 262 of FIG. 2B may correspond to the display 1400 of FIG. 1.

The user input receiving unit 264 may receive, through a gain setting window, a user input for adjusting at least one selected from the sizes and number of slide bars. For example, the user input receiving unit 264 may include a keypad, a mouse, a touch pad, a touch screen, a trackball, and a jog switch, but is not limited thereto. The user input receiving unit 264 may include another input device. The user input receiving unit 264 of FIG. 2B may correspond to the input device 1600.

When an external device operates in connection with the ultrasound image providing apparatus 200, the controller 220 may perform control to display a gain setting window on an interface of the external device. The controller 220 may adjust at least one selected from the sizes and number of slide bars displayed by the interface of the external device.

Figure 3:
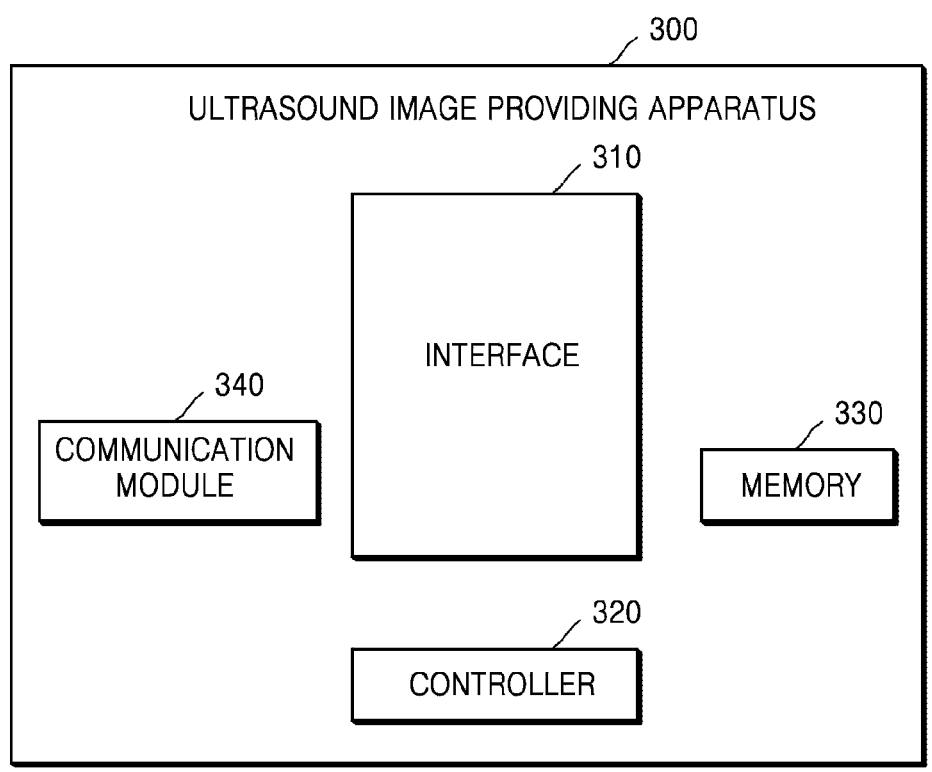
FIG. 3 is a block diagram for describing an ultrasound image providing apparatus according to another exemplary embodiment.

FIG. 3 is a block diagram for describing an ultrasound image providing apparatus 300 according to another exemplary embodiment.

In comparison with the ultrasound image providing apparatus 200 described above with reference to FIG. 2A, the ultrasound image providing apparatus 300 includes a memory 330 and a communication module 340, and the other elements are the same as those of the ultrasound image providing apparatus 200.

In detail, a user interface 310 and a controller 320 of the ultrasound image providing apparatus 300 correspond to the interface 210 and controller 220 of the ultrasound image providing apparatus 200 of FIG. 2A, respectively. Thus, the same descriptions provided with regard to the ultrasound image providing apparatus 200 of FIG. 2 are not repeated.

The memory 330 may store various data associated with an ultrasound image. In detail, the memory 330 may store a captured ultrasound image. Also, the memory 330 may store information about at least one selected from the sizes and number of slide bars for setting a plurality of TGC values. For example, the memory 330 may store information about a size of a screen displayed by a display and information about the sizes and number of slide bars corresponding to the size of the screen. When the ultrasound image providing apparatus 300 is included in and operated by the ultrasound diagnosis apparatus 1000 of FIG. 1, the memory 330 of FIG. 3 may correspond to the memory 1500 of FIG. 1.

Moreover, the communication module 340 may transmit or receive data to or from an external device over a wired/wireless network. For example, when the ultrasound image providing apparatus 300 is included in and operated by the ultrasound diagnosis apparatus 1000 of FIG. 1, the communication module 340 corresponds to the communication module 1300 of FIG. 1. In this case, the communication module 340 may transmit or receive data to or from the external server 32, the medical apparatus 34, and the portable terminal 36.

Moreover, the user interface 310 may be of the same type as that of the interface 210 of FIG. 2A. Therefore, for describing the user interface 310, the same descriptions provided with regard to the interface 210 of FIG. 2A are not repeated.

FIG. 4A is a diagram for describing the interface 210 which displays a screen including a gain setting window.

Referring to FIG. 4A, each of the ultrasound image providing apparatuses 200 and 300 may be implemented as the portable ultrasound image providing apparatus 400a. The portable ultrasound image providing apparatus 400a may include, for example, a PACS viewer, a smartphone, a laptop computer, a PDA, or a tablet PC.

Referring to FIG. 4A, the interface 210 may include the display 450 of the portable ultrasound image providing apparatus 400a. According to an exemplary embodiment, the display 450 may display a screen that includes an ultrasound image 401 and a gain setting window 403.

Referring to FIG. 4B, each of the ultrasound image providing apparatuses 200 and 300 may be implemented as the cart-type ultrasound image providing apparatus 400b.

According to an exemplary embodiment illustrated in FIG. 4B, the interface 210 may include the display 404 that displays an ultrasound image provided by the cart-type ultrasound image providing apparatus 400b. The display 404 may display a screen that includes an ultrasound image 440 and a gain setting window 430. In detail, as illustrated in FIG. 4B, the display 404 may display a screen in which the ultrasound image 440 and the gain setting window 430 are arranged in parallel. Also, although not shown, the display 404 may display a screen in which the ultrasound image 440 and the gain setting window 430 are shown to overlap each other. The controller 220 may perform control to change and display at least one selected from the sizes and number of slide bars according to a size of the display 404.

Figure 4D:
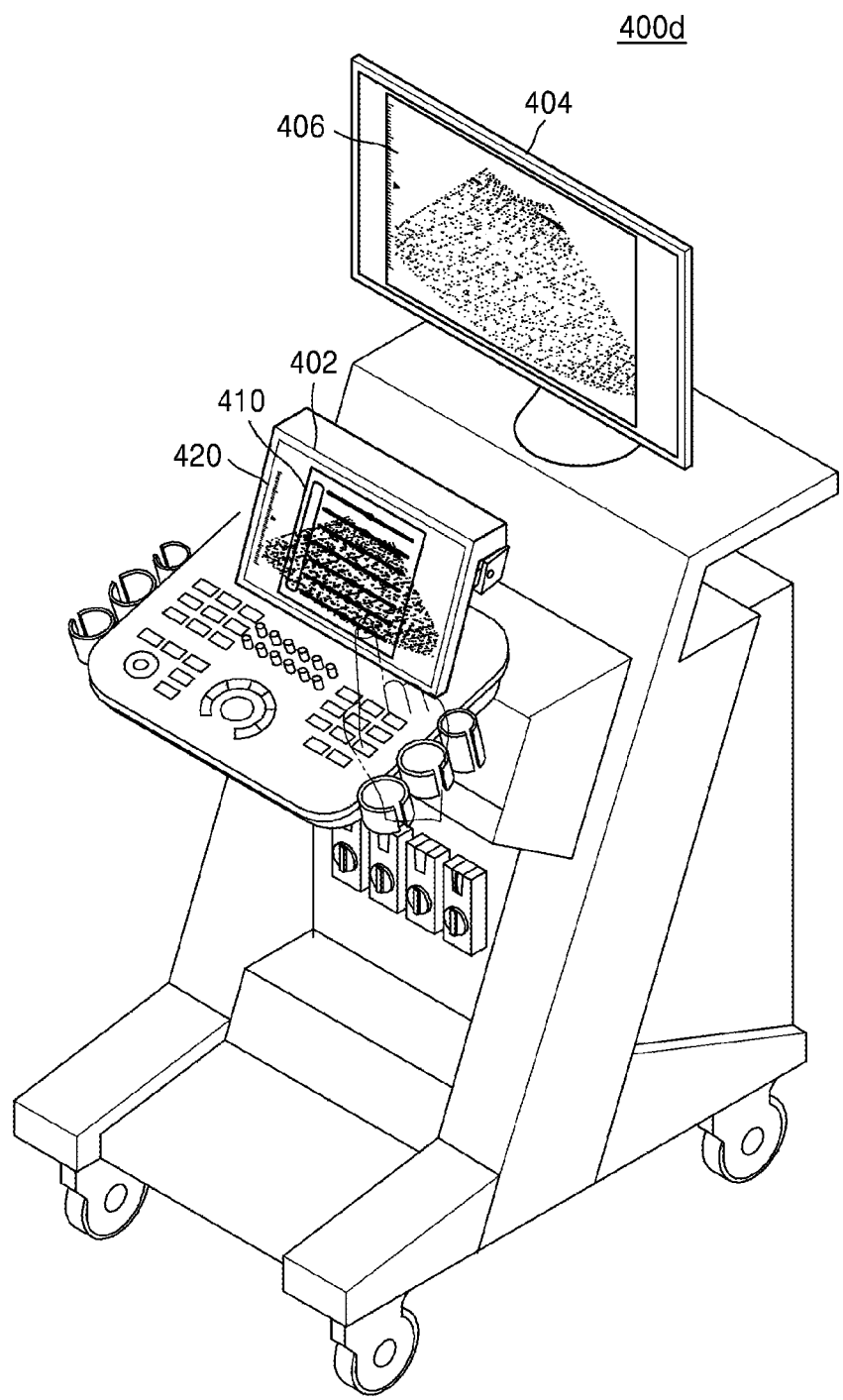

According to another exemplary embodiment illustrated in FIGS. 4C and 4D, the interface 210 may include the display 402 that is provided in the control panel of the cart-type ultrasound image providing apparatus 400c separately from a display 404.

Referring to FIG. 4C, the display 404 may display a screen including an ultrasound image 406. Also, the display 402 provided in the control panel may display a screen that includes an ultrasound image 412 and a gain setting window 410.

In detail, as illustrated in FIG. 4C, the display 402 of the control panel may display a screen in which the ultrasound image 412 and the gain setting window 410 are arranged in parallel. Also, as illustrated in FIG. 4D, the display 402 of the control panel may display a screen in which an ultrasound image 420 and the gain setting window 410 are shown to overlap each other. The controller 220 may perform control to change and display at least one selected from the sizes and number of slide bars according to a size of the display 402.

The ultrasound image 412 displayed on the screen of the display 402 of the control panel of FIG. 4C may correspond to the ultrasound image 406 of the display 404. Likewise, an ultrasound image 420 displayed on the screen of the display 402 of the control panel of FIG. 4D may correspond to an ultrasound image 406 of the display 404. Also, the display 402 may display a screen, which includes a virtual ultrasound image, instead of a screen including an actual ultrasound image.

According to the exemplary embodiments illustrated in FIGS. 4A to 4D, a user may intuitively recognize which depth of an ultrasound image a TGC value that is capable of being set in each slide bar is a TGC value for.

Figure 4E:
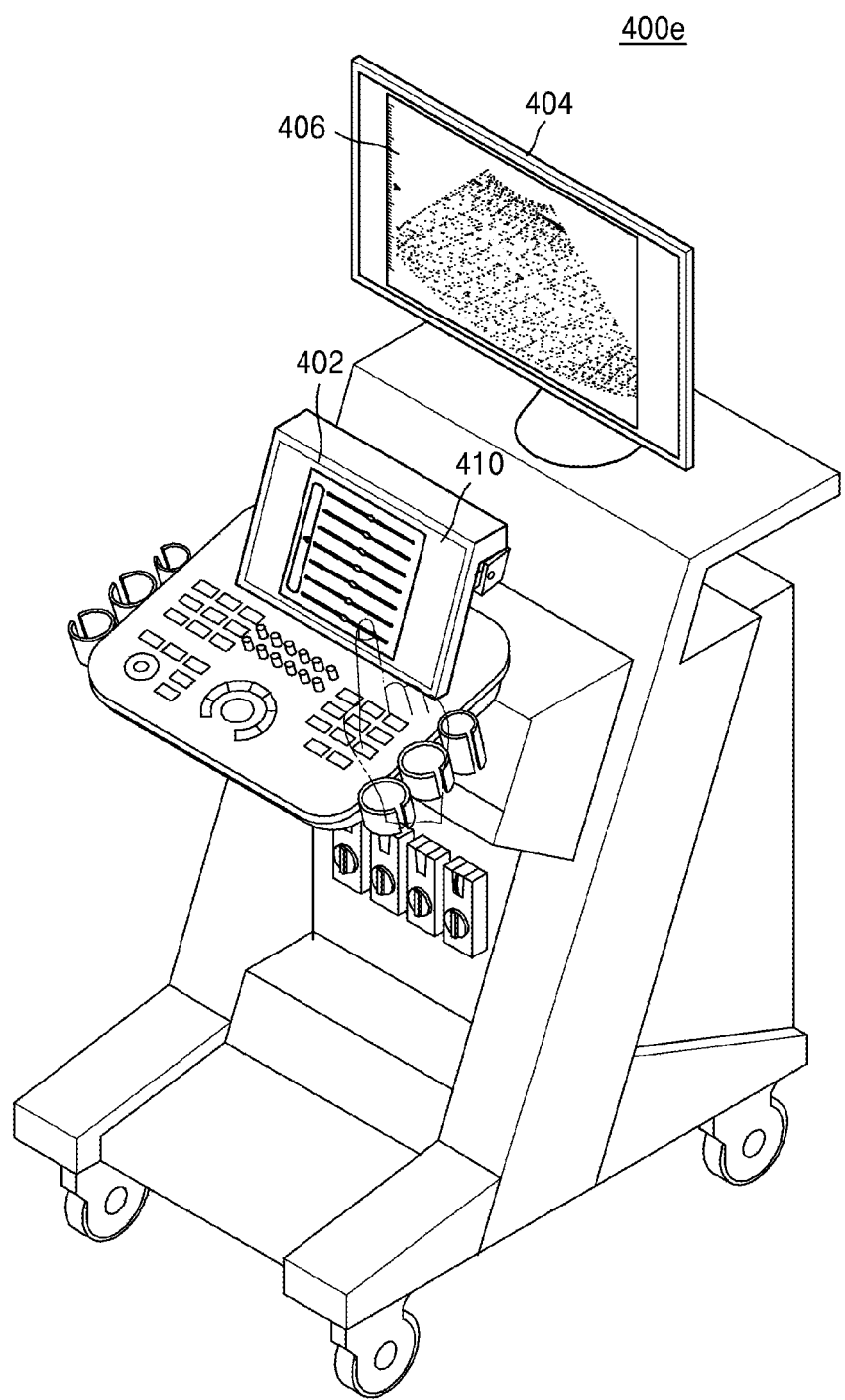

According to an exemplary embodiment illustrated in FIG. 4E, the interface 210 may include a display 402 that is provided in a control panel of a cart-type ultrasound image providing apparatus 400e. The display 402 of the control panel may display a screen including only a gain setting window 410.

In FIGS. 4A to 4E, an exemplary embodiment in which the interface 210 provides a screen including a gain setting window has been described above. Hereinafter, exemplary embodiments in which a user input is received and a gain setting window is updated and displayed through the interface 210 will be described.

FIGS. 5 to 8 are diagrams for describing a gain setting window according to exemplary embodiments.

FIG. 5 illustrates an exemplary embodiment of a user input which increases a length of a slide bar of a gain setting window 510.

Figure 5A:
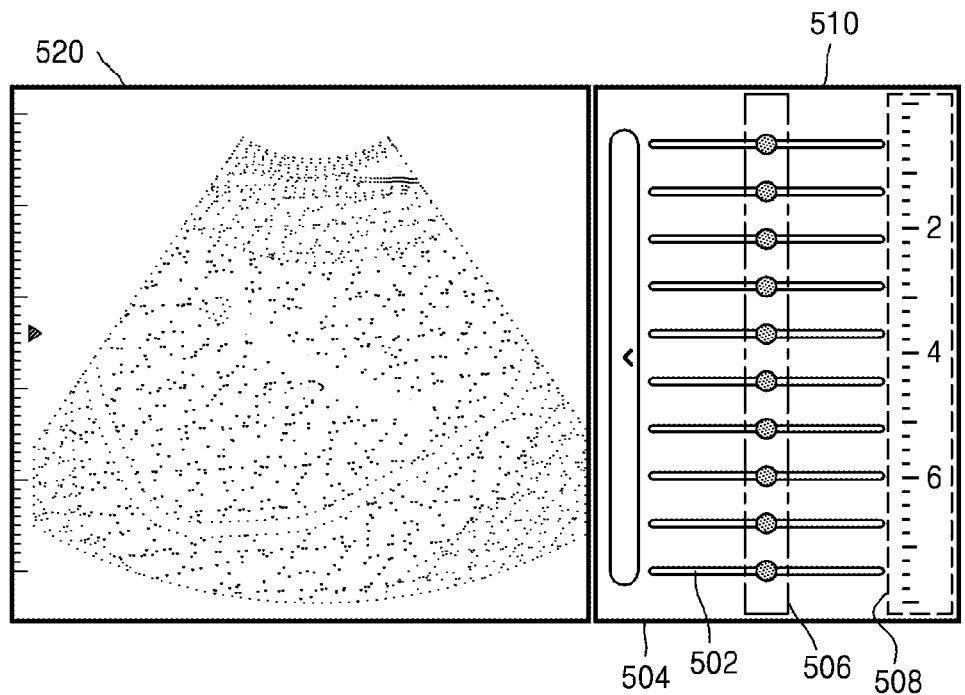
FIG. 5A-FIG. 5B illustrates an exemplary embodiment of a user input which increases a length of a slide bar of a gain setting window.

FIG. 5A illustrates a screen that includes the gain setting window 510 and an ultrasound image 520 in which a TGC value is set through the gain setting window 510.

The gain setting window 510 may include a plurality of slide bars 502. For example, the gain setting window 510 may include eight or ten slide bars, but the number of slide bars is not limited thereto. A plurality of adjustment buttons 506 may be displayed on the plurality of slide bars 502, respectively. A gradation 508 indicating a depth value of an ultrasound image, corresponding to a TGC value which is set by each of a plurality of slide bars, may be displayed on the right of the slide bar 502. A button 504 for receiving a user input, which increases or decreases a horizontal-direction length of each of a plurality of slide bars, may be displayed on the left of the slide bar 502.

Figure 5B:
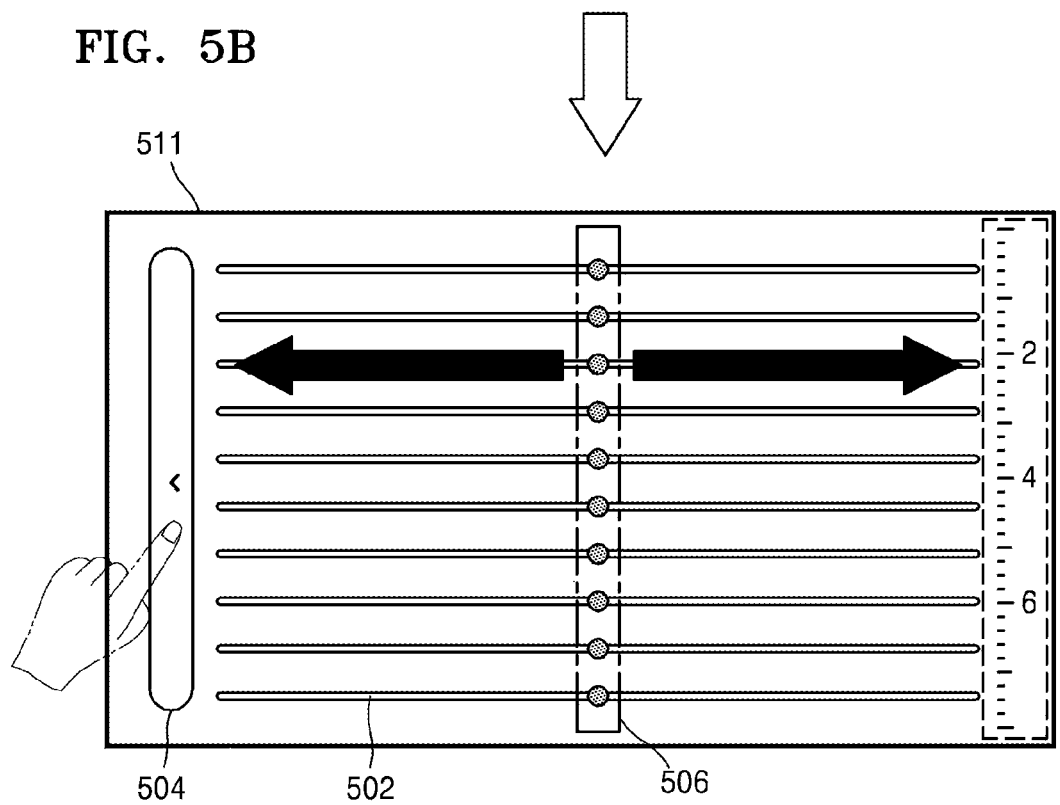

FIG. 5B illustrates an example of a gain setting window 511 which has been updated after a user input which increases a horizontal-direction length of each of a plurality of slide bars is received through a gain setting window 511.

For example, as illustrated in FIG. 5B, a user may touch and drag the button 504 to a certain position. The ultrasound image providing apparatus 200 may increase or decrease a horizontal-direction length of each of a plurality of slide bars included in the gain setting window 510, based on a user input. For example, as illustrated in FIG. 5B, the ultrasound image providing apparatus 200 may increase a horizontal-direction length of each of a plurality of slide bars so as to correspond to a distance by which the user has touched and dragged the button 504. Also, the horizontal-direction length of each of the plurality of slide bars may be adjusted based on the number of times the user touches the button 504, a touched intensity, and a touch time.

Moreover, one screen includes the ultrasound image 520 and the gain setting window 510, and when a size of the gain setting window 510 increases or decreases, the controller 210 may decrease or increase a size of the ultrasound image 520 in response to the increase or decrease in the size of the gain setting window 510. For example, as illustrated in FIG. 5B, when a size of the updated gain setting window 511 increases, the controller 210 may decrease the size of the ultrasound image 520 so that the updated gain setting window 511 and the ultrasound image 520 are included in one screen.

When the size of the gain setting window 510 increases to a certain size or more, the controller 210 may remove the ultrasound image 520 included in a screen and output a screen including only the gain setting window 510. When the gain setting window 510 is updated based on a user input, the ultrasound image providing apparatus 200 may update positions of the plurality of adjustment buttons 506 displayed on a plurality of slide bars. The positions of the plurality of adjustment buttons 506 displayed on the plurality of slide bars may correspond to a plurality of TGC values which are set in data of the ultrasound image 520. Also, although not shown, the ultrasound image providing apparatus 200 may display, as numbers, a plurality of TGC values respectively corresponding to a plurality of slide bars.

As illustrated in FIG. 5B, by increasing a horizontal-direction length of each of a plurality of slide bars, the user precisely controls a TGC value of the ultrasound image 520.

FIG. 6 illustrates an exemplary embodiment of a user input which increases the number of slide bars included in a gain setting window 610.

Figure 6A:
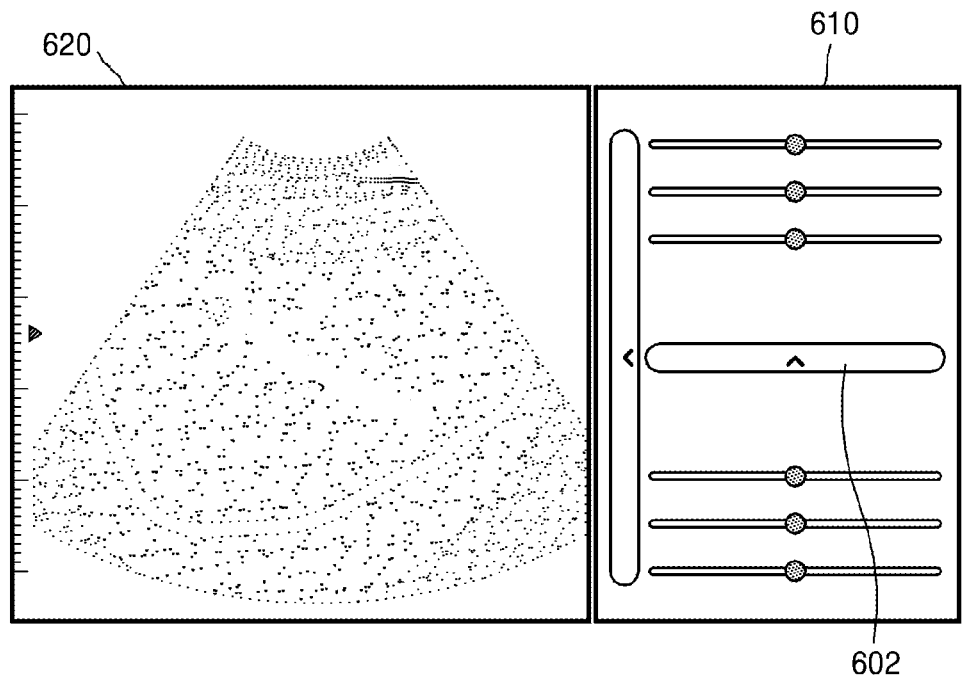
FIG. 6A-FIG. 6B illustrates an exemplary embodiment of a user input which increases the number of slide bars included in a gain setting window.

FIG. 6A illustrates a screen that includes the gain setting window 510 and an ultrasound image 620 in which a TGC value is set through the gain setting window 610. For describing the gain setting window 610 of FIG. 6, the same descriptions provided with regard to the gain setting window 510 of FIG. 5 are not repeated. The gain setting window 610 may display a button 602 for receiving a user input which increases or decreases the number of slide bars.

Figure 6B:
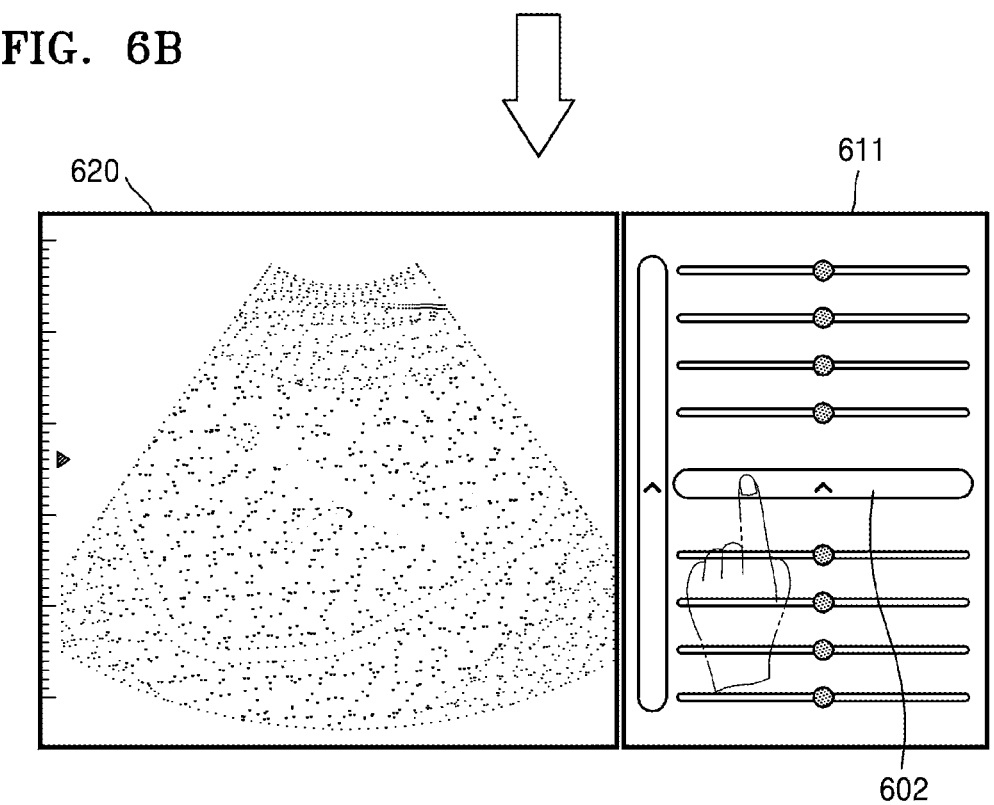

FIG. 6B illustrates an example of a gain setting window 611 which has been updated after a user input which increases the number of slide bars is received through the gain setting window 610.

For example, a user may increase the number of slide bars by tapping or pressing the button 602. As another example, the user may decrease the number of slide bars by double tapping the button 602. When the gain setting window 610 is updated based on a user input, the ultrasound image providing apparatus 200 may update digits of a plurality of TGC values displayed on a plurality of slide bars.

As illustrated in FIG. 6B, by increasing the number of slide bars, the user may more finely segment a depth of the ultrasound image 620 to adjust a TGC value.

FIG. 7 illustrates an exemplary embodiment of an input which increases the number of slide bars in a first section 730 of a gain setting window 710.

Figure 7A:
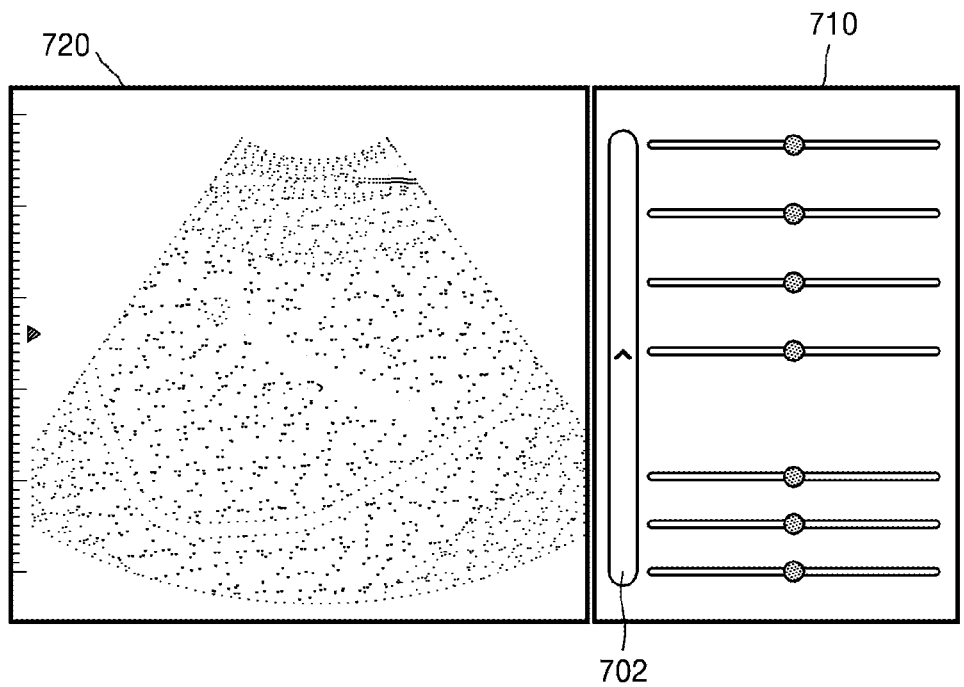
FIG. 7A-FIG. 7B illustrates an exemplary embodiment of an input which increases the number of slide bars in a first section of a gain setting window.

FIG. 7A illustrates a screen that includes the gain setting window 710 and an ultrasound image 720 in which a TGC value is set through the gain setting window 710. For describing the gain setting window 710 of FIG. 7, the same descriptions provided with regard to the gain setting window 510 of FIG. 5 are not repeated. The gain setting window 710 may display a button 702 for receiving a user input which increases or decreases the number of slide bars in the first section 730. The first section 730 may set by a user input.

Figure 7B:
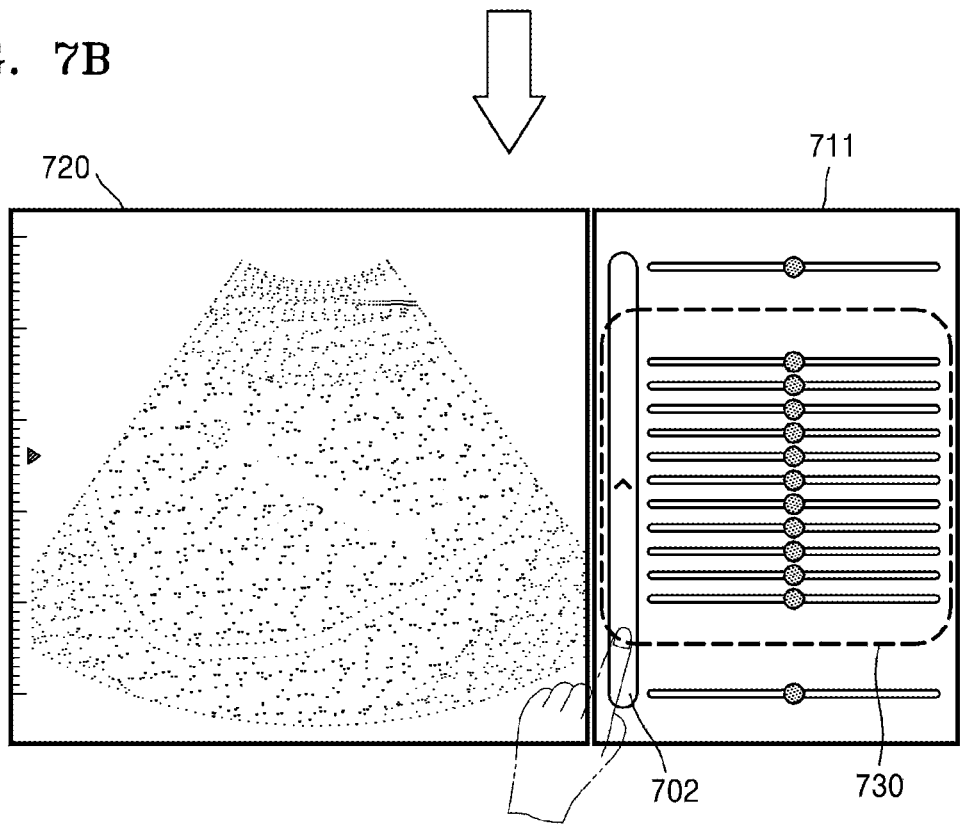

FIG. 7B illustrates an example of a gain setting window 711 which has been updated after a user input which increases the number of slide bars in the first section 730 is received.

For example, a user may increase the number of slide bars in the first section 730 by tapping or pressing the button 702. Also, the user may decrease the number of slide bars by double tapping the button 702.

When the user desires to finely adjust a TGC value corresponding to the first section 730 of the ultrasound image 720, as illustrated in FIG. 7B, the user segments and controls the TGC value by increasing the number of slide bars in the first section 730.

Figure 8:
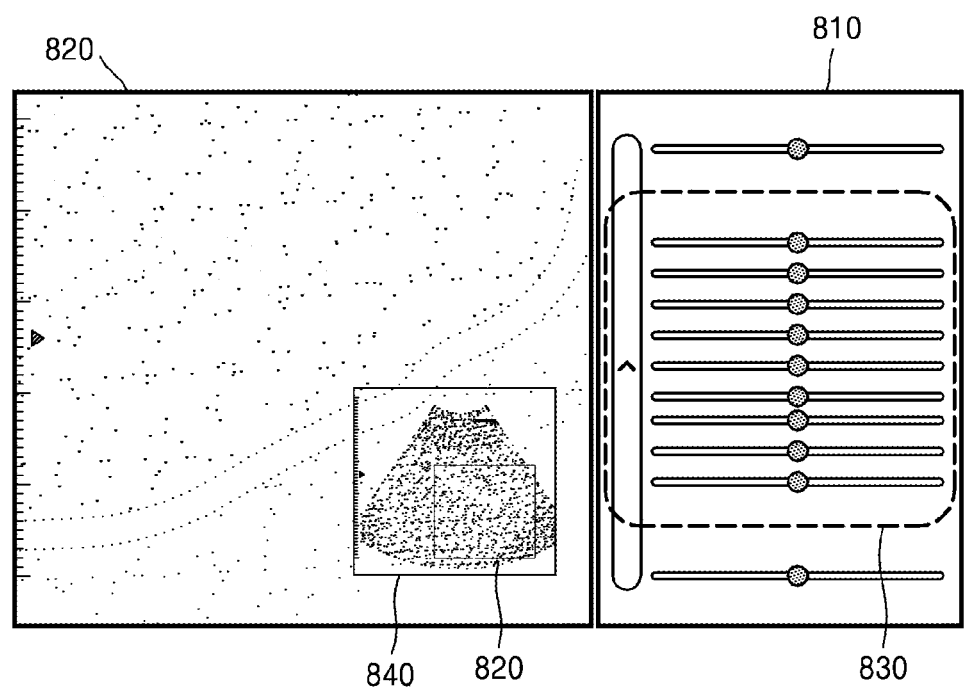
FIG. 8 illustrates an exemplary embodiment for increasing the number of slide bars in a first section of a gain setting window when a zoom input is received.

FIG. 8 illustrates an exemplary embodiment for increasing the number of slide bars in a first section 830 of a gain setting window 810 when a zoom input is received.

FIG. 8 illustrates a screen which includes the gain setting window 810 and an enlarged ultrasound image 820. The enlarged ultrasound image 820 is an image which has been enlarged based on a zoom input of a user. A before-enlargement ultrasound image 840 and a portion 842 corresponding to the enlarged ultrasound image 820 may be displayed in the enlarged ultrasound image 820. As illustrated in FIG. 8, when the ultrasound image providing apparatus 200 receives the zoom input of the user, the number of slide bars may increase in the first section 830 corresponding to a zoomed portion.

When the user desires to finely adjust a TGC value of a certain portion of the ultrasound image 820, the user may segment and control the TGC value by enlarging the ultrasound image 820 and simultaneously increasing the number of slide bars in the first section 830 corresponding to the enlarged portion 842.

Figures 9A, 9B:
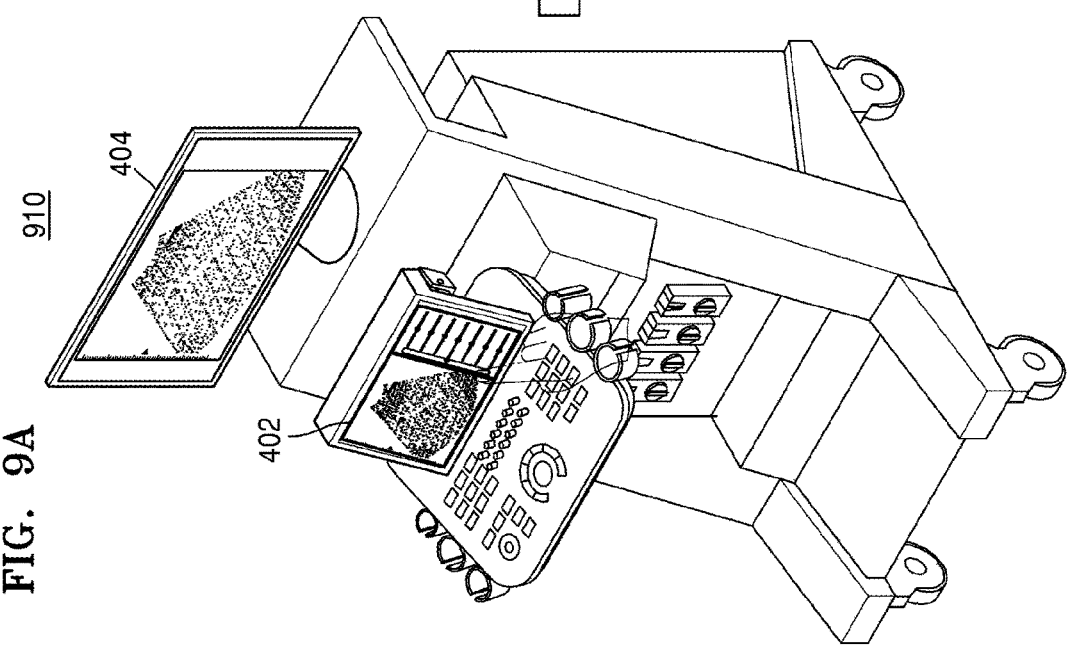
FIG. 9A-FIG. 9B illustrates an exemplary embodiment of a case in which ultrasound image data is supplied from a cart-type ultrasound image providing apparatus to a portable ultrasound image providing apparatus.

FIG. 9 illustrates an exemplary embodiment of a case in which ultrasound image data is supplied from a cart-type ultrasound image providing apparatus to a portable ultrasound image providing apparatus.

Referring to FIG. 9, a cart-type ultrasound image providing apparatus 910 may include a display 404 and a display 402 which is provided in a control panel. For example, a user may check ultrasound images respectively displayed by the display 402 and display 404 of the cart-type ultrasound image providing apparatus 910. Subsequently, the user may transmit ultrasound image data from the cart-type ultrasound image providing apparatus 910 to a portable terminal 920. A display 950 included in the portable terminal 920 may be of a type which differs from that of the display 402 and the display 404. When the transmitted ultrasound image data is displayed on the portable terminal 920, a size of an ultrasound image 901 and a size of a gain setting window 903 may be adjusted according to a type of the display 950 of the portable terminal 920. Also, the cart-type ultrasound image providing apparatus 910 may adjust at least one selected from the sizes and number of slide bars included in the gain setting window 903.

For example, a size of the display 950 of FIG. 9 may be smaller than that of the display 402. In this case, the number of slide bars included in the gain setting window 903 may be adjusted to be less than the number of slide bars included in a gain setting window displayed by the display 402.

Moreover, the display 950 of FIG. 9 may display a screen in which the ultrasound image 901 and the gain setting window 903 are arranged in parallel. In this case, a size of the ultrasound image 901 and a size of the gain setting window 903 may be smaller than a size of an ultrasound image displayed by the display 404 and a size of a gain setting window displayed by the display 402. Likewise, the number of slide bars included in the gain setting window 903 may be adjusted to be less than the number of slide bars included in the gain setting window displayed by the display 402.

Figure 10:
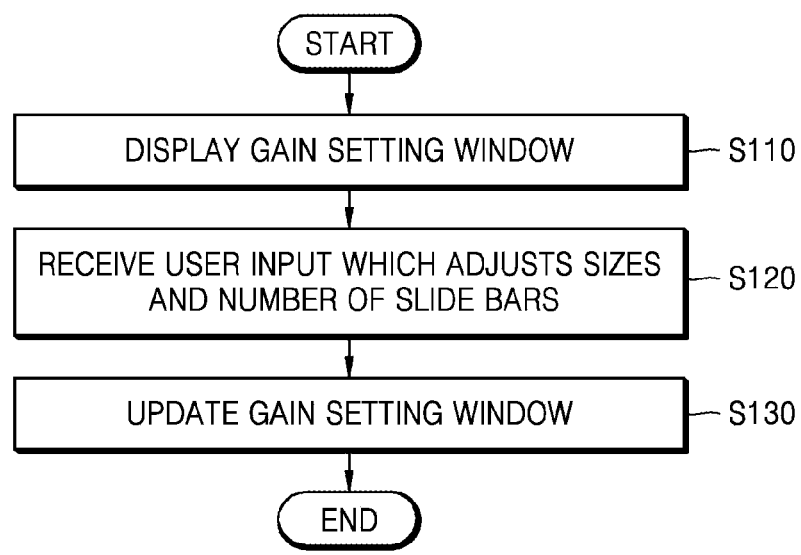
FIG. 10 is a flowchart illustrating an ultrasound image providing method according to an exemplary embodiment.

FIG. 10 is a flowchart illustrating an ultrasound image providing method according to an exemplary embodiment.

The ultrasound image providing method according to an exemplary embodiment may be performed by the above-described ultrasound image providing apparatus 200 (300).

In operation S110, the ultrasound image providing apparatus 200 (300) may display a screen including a gain setting window which includes a plurality of slide bars for setting a plurality of TGC values of ultrasound image data.

In operation S120, the ultrasound image providing apparatus 200 (300) may receive, through the gain setting window, a user input for adjusting at least one selected from the sizes and number of slide bars.

In operation S130, the ultrasound image providing apparatus 200 (300) may perform control to update and display the gain setting window, based on the user input.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound image providing apparatus comprising:
a display; and
a controller configured to:
control the display to display an ultrasound image and a screen including a gain setting window which includes a plurality of slide bars for setting a plurality of time gain compensation (TGC) values of ultrasound image data;
control the display to display a button with the plurality of slide bars;
receive a user input for adjusting at least one selected from sizes and a number of the plurality of slide bars; and
control the display to update and display the gain setting window, based on the user input,
wherein the controller is further configured to, in response to a zoom input, display a zoom portion of the ultrasound image in a zoomed-in state, and increase a horizontal direction length or a number of slide bars for setting TGC values for the zoom portion.

2. The ultrasound image providing apparatus of claim 1, wherein, on the plurality of slide bars, a position of each of a plurality of adjustment buttons corresponds to a TGC value.

3. The ultrasound image providing apparatus of claim 1, wherein the display comprises a touch screen.

4. The ultrasound image providing apparatus of claim 1, wherein,
the gain setting window comprises the plurality of slide bars which are arranged along a vertical axis, and
the vertical axis indicates a depth of the ultrasound image.

5. The ultrasound image providing apparatus of claim 4, wherein the controller receives a user input for increasing or decreasing a horizontal-direction length of each of the plurality of slide bars.

6. The ultrasound image providing apparatus of claim 4, wherein the controller receives a user input for increasing or decreasing the number of slide bars.

7. The ultrasound image providing apparatus of claim 6, wherein the controller receives a user input for increasing or decreasing the number of slide bars in a certain section of the vertical axis.

8. The ultrasound image providing apparatus of claim 6, wherein, the controller receives a user input for enlarging and displaying the ultrasound image, and the controller performs control to increase and display the number of slide bars.

9. The ultrasound image providing apparatus of claim 1, wherein the controller performs control to change and display at least one selected from the sizes and the number of slide bars according to a size of an interface on the display.

10. The ultrasound image providing apparatus of claim 1, wherein the plurality of TGC values respectively corresponding to the plurality of slide bars are displayed as numbers.

11. The ultrasound image providing apparatus of claim 10, wherein, when the gain setting window is updated based on the user input, the processor updates the plurality of TGC values respectively displayed on the plurality of slide bars.

* * * * *